United States Patent [19]

Priddy

[11] 3,935,243

[45] Jan. 27, 1976

[54] METHOD FOR PREPARING POLYPEROXYDICARBONATE ESTERS

[75] Inventor: Duane B. Priddy, Coleman, Mich.

[73] Assignee: The Dow Chemical Company, Midland, Mich.

[22] Filed: Sept. 30, 1974

[21] Appl. No.: 510,181

Related U.S. Application Data

[63] Continuation-in-part of Ser. No. 398,046, Sept. 17, 1973, abandoned.

[52] U.S. Cl. .................................................. 260/463
[51] Int. Cl.² ..................... C07C 68/00; C07C 69/96
[58] Field of Search ..................................... 260/463

[56] References Cited

OTHER PUBLICATIONS

Strain, et al., *J.A.C.S.*, 72 (1950), pp. 1254–1263.

*Primary Examiner*—Joseph Paul Brust
*Attorney, Agent, or Firm*—Glwynn R. Baker

[57] ABSTRACT

Dialkyl alkylenebis(peroxydicarbonates) and oxyalkylenebis(peroxydicarbonates) and corresponding higher polyfunctional peroxydicarbonic acid esters are useful initiators of vinyl polymerization. These compounds are prepared by reacting a sodium alkylperoxycarbonate with a diol bis(chloroformate) at from about −10°C to about 20°C.

8 Claims, No Drawings

METHOD FOR PREPARING POLYPEROXYDICARBONATE ESTERS

CROSS REFERENCE TO RELATED APPLICATIONS

This Application is a continuation-in-part of my previously filed application Ser. No. 398,046, filed Sept. 17, 1973, now abandoned, entitled Peroxydicarbonate Esters.

BACKGROUND OF THE INVENTION

A great number of compounds are known which contain one or more peroxide linkages within the molecule. Many of these have been used to generate free radicals by their decomposition under varying conditions depending upon their thermal or chemical stability. Several kinds of peroxyacid derivatives have been used in this way, often to initiate the polymerization of ethylenically unsaturated monomers. Peracetates, persulfates, and benzoyl peroxide are examples of some of these.

SUMMARY OF THE INVENTION

The organic peroxydicarbonates which can be prepared in accordance with the present invention are those which have the general formula

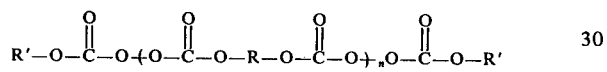

wherein R' is an alkyl radical of 1-6 carbon atoms, R is an alkylene radical of 2-8 carbon atoms or a polyalkyleneoxy radical wherein each alkylene group has 2-4 carbon atoms and R has a maximum of about 12 carbon atoms, and n is an integer, preferably 1-4.

These compounds are readily prepared by reacting sodium alkyl peroxycarbonate, with a diol bis(chloroformate). The sodium alkylperoxycarbonate is conveniently prepared by reacting sodium peroxide with an alkyl chloroformate. The relative proportions of reactants determine whether a bis(peroxydicarbonate), a tris(peroxydicarbonate), or a higher polyfunctional peroxydicarbonate is the product. To make a bis(peroxydicarbonate), the intermediate peroxycarbonate is reacted with the diol bischloroformate using at least the theoretical two moles of intermediate, preferably in excess of two moles, per mole of diol bischloroformate. In making a tris(peroxydicarbonate), two moles of diol bischloroformate is reacted with the same quantity of peroxycarbonate intermediate plus about a mole of sodium peroxide. Higher polyfunctional peroxydicarbonates are produced by increasing the proportions of chloroformate and peroxide according to the empirical equation for the overall process:

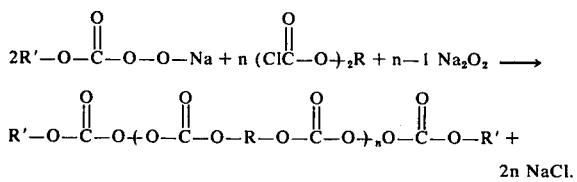

The reaction is carried out at from about −10°C to about 20°C, preferably in aqueous lower alkanol. The peroxydicarbonate product is conveniently separated by extraction of the reaction mixture with a low boiling solvent such as ether or a lower alkane fraction which then is easily evaporated from the extract to obtain the peroxydicarbonate product as the residue. The products are isolated as colorless oils which are stable when stored below about 12°C.

In this way, bis(peroxydicarbonates) are prepared by reacting sodium peroxide with an alkyl chloroformate such as methyl chloroformate, ethyl chloroformate, tert-butyl chloroformate, or hexyl chloroformate to make the intermediate sodium alkyl peroxycarbonate. This intermediate is then reacted with the bischloroformate of a diol as defined above, illustrative diols being ethylene glycol, propylene glycol, trimethylene glycol, butylene glycol, 1,6-hexanediol, diethylene glycol, triethylene glycol, dipropylene glycol, dibutylene glycol, and 2,5-dimethyl-2,5-hexanediol. In order to make a tris(peroxydicarbonate) as defined, the sodium alkyl peroxycarbonate is reacted with the diol bischloroformate in the presence of sodium peroxide or other such peroxide using the proportions previously described.

DETAILED DESCRIPTION

Example 1

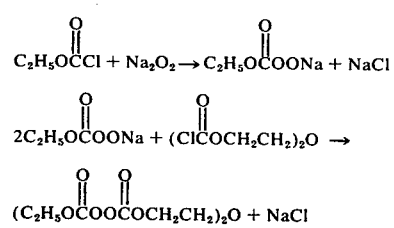

A solution of 8.0 g. (0.1 mole) $Na_2O_2$ in 75 ml. of cold water was cooled while it was diluted with 50 ml. of methanol. Cooling was continued while 10 g. (0.09 mole) of ethyl chloroformate was added over 10 minutes. The reaction mixture was stirred at 0° to 5°C. for another ten minutes and then 5 g. (0.025 mole) of diethylene glycol bischloroformate was added over 15 minutes at −10°C. The mixture was stirred for an additional 15 minutes at −10° to 0°C. and then it was extracted with ether at 0°C. The ether extract was dried over anhydrous sodium sulfate and evaporated under nitrogen at 0°C. to yield 4 g. of clear colorless oil. This product was identified as oxydiethylenebis(ethyl peroxydicarbonate) by treating a sample with aqueous sodium iodide and titrating the liberated iodine.

EXAMPLE 2

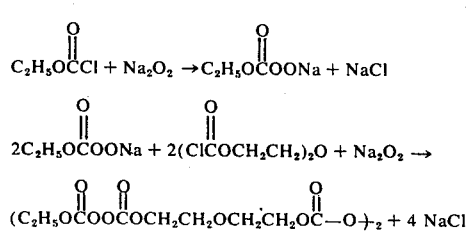

The proportions of the reactants of the foregoing example were varied to obtain the corresponding trifunctional peroxydicarbonate ester. A solution of 24 g. (0.6 mole) NaOH in a mixture of 250 ml. of water and 150 ml. of methanol was cooled to 5°C. and 34 g. (0.3 mole) of 30% $H_2O_2$ was added. The cooled solution was stirred while 20 g. (0.18 mole) of ethyl chloroformate was added and stirring was continued for an additional 30 minutes. At this point, 20 g. (0.09 mole) of diethylene glycol bischloroformate was added dropwise over a period of 30 minutes while maintaining the temperature of the reaction mixture at 5°C. The mixture was stirred for another 30 minutes at the same temperature and then it was extracted with cold benzene. The benzene extract was dried and evaporated as before to obtain 8 g. of clear, colorless oil which was identified by iodine titration and by nuclear magnetic resonance analysis as the diethyl ester of bis(diethylene glycol) tris(peroxydicarbonate).

EXAMPLE 3

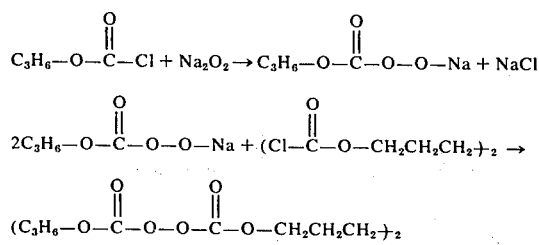

A solution of 16 g. (0.2 mole) of $Na_2O_2$ in a mixture of 150 ml. of water and 100 ml. of methanol was maintained at 5° to 10°C. while 20 g. of isopropyl chloroformate was added dropwise over 15 minutes and the final mixture was stirred for another 15 minutes at that temperature. Then 10 g. (0.04 mole) of 1,6-hexanediol bis(chloroformate) was added in 15 minutes and the mixture was stirred for an hour at 5° to 10°C. The reaction mixture was extracted with ether and the extract evaporated as in Example 1 to obtain 9 g. of clear, colorless oil. This was identified by iodine titration as the expected diisopropyl ester of hexamethylenebis(peroxydicarbonate).

Using the procedure described in Examples 1–3, sodium alkyl peroxycarbonates are prepared and reacted with the bischloroformates of aliphatic diols as previously defined to obtain the dialkyl esters of the corresponding bisperoxydicarbonates. By including sodium peroxide or other such inorganic peroxide and varying the molar proportions of this and the diol bischloroformate according to the empirical equation set forth above, trisperoxydicarbonates, tetrabisperoxydicarbonates, and higher polyfunctional peroxydicarbonates are obtained as desired. For practical reasons, proportions of reactants are limited to those required to make polyperoxydicarbonates where $n$ in the general formula has a maximum value of four. Compounds with a higher value of $n$ can of course be prepared, but problems of completing the reaction and practical isolation of a reasonably uniform product make these materials of only theoretical interest.

I claim:

1. A process for preparing compounds having the formula

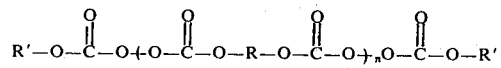

wherein R' is an alkyl radical of 1–6 carbon atoms, R is an alkylene radical of 2–8 carbon atoms or a polyalkyleneoxy radical wherein each alkylene group has 2–4 carbon atoms and R has a maximum of about 12 carbon atoms, and n is an integer of at least 2, which comprises reacting sodium peroxide with an alkyl chloroformate of the formula

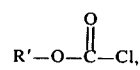

wherein R' has the aforesaid significance, to form the sodium alkylperoxy carbonate

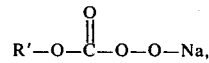

reacting a sodium alkyperoxycarbonate with a diol bis(chloroformate) of the formula

wherein R has the aforesaid significance, to form the corresponding peroxydicarbonate, said reaction being carried out at about −10°C. to about 20°C. in the presence of an aqueous lower alkanol.

2. The process of claim 1 wherein said sodium alkylpercarbonate is prepared by reacting sodium peroxide with an alkyl chloroformate of the formula

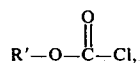

wherein R' is ethyl to form the sodium ethylperoxycarbonate

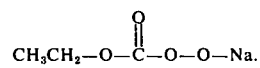

3. The process of claim 1 wherein the reactions are carried out at between about 0° and 10°C. in aqueous methanol.

4. The process of claim 1 wherein R' is isopropyl and R is hexamethylene.

5. The process of claim 1 wherein R' is ethyl and R is oxydiethylene.

6. A process for preparing compounds having the formula

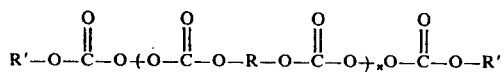

wherein R' is an alkyl radical of 1–6 carbon atoms, R is an alkylene radical of 2–8 carbon atoms or a polyalkyleneoxy radical wherein each alkylene group has 2–4 carbon atoms and R has a maximum of about 12 carbon atoms, and n is an integer from 2 to 4 which comprises reacting sodium peroxide with an alkyl chloroformate of the formula

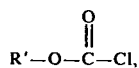

wherein R' has the aforesaid significance, to form the sodium alkylperoxycarbonate

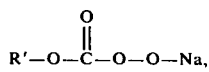

reacting sodium alkylperoxycarbonate with at least two moles to about four moles of a diol bis(chloroformate) of the formula

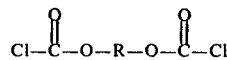

wherein R has the aforesaid significance, to form the corresponding peroxydicarbonate, said reaction being carried out at about −10°C. to about 20°C. in the presence of an aqueous lower alkanol and in the presence of additional peroxide.

7. The process of claim 6 wherein said sodium alkylpercarbonate is prepared by reacting sodium peroxide with an alkyl chloro formate of the formula

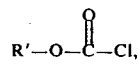

wherein R' is ethyl to form the sodium ethylperoxycarbonate

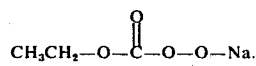

8. The process of claim 6 wherein said diol bis(chloroformate) is present in at least three moles; R' is ethyl and R is oxydiethylene.

* * * * *